US009221699B2

(12) United States Patent
Scalzi et al.

(10) Patent No.: US 9,221,699 B2
(45) Date of Patent: Dec. 29, 2015

(54) INHIBITION OF METHANE PRODUCTION DURING ANAEROBIC REDUCTIVE DECHLORINATION

(71) Applicant: Innovative Environmental Technologies, Inc., Pipersville, PA (US)

(72) Inventors: Michael Scalzi, Doylestown, PA (US); Antonis Karachalios, North Wales, PA (US)

(73) Assignee: Innovative Environment Technologies, Inc., Pipersville, PA (US)

( * ) Notice: Subject to any disclaimer, the term of this patent is extended or adjusted under 35 U.S.C. 154(b) by 71 days.

(21) Appl. No.: 13/785,840

(22) Filed: Mar. 5, 2013

(65) Prior Publication Data

US 2014/0251900 A1  Sep. 11, 2014

(51) Int. Cl.
*C02F 3/34* (2006.01)
*B09C 1/08* (2006.01)
*C02F 101/32* (2006.01)
*C02F 101/36* (2006.01)
*C02F 103/06* (2006.01)

(52) U.S. Cl.
CPC . *C02F 3/342* (2013.01); *B09C 1/08* (2013.01); *C02F 3/344* (2013.01); *B09C 2101/00* (2013.01); *C02F 2101/322* (2013.01); *C02F 2101/36* (2013.01); *C02F 2103/06* (2013.01); *C02F 2305/06* (2013.01)

(58) Field of Classification Search
USPC ......... 210/610–611, 631, 747.1, 747.7, 747.8
See application file for complete search history.

(56) References Cited

U.S. PATENT DOCUMENTS

| | | | |
|---|---|---|---|
| 5,648,258 A | 7/1997 | Odom | |
| 5,788,857 A | 8/1998 | Yang et al. | |
| 5,985,907 A * | 11/1999 | Wolin et al. | 514/408 |
| 6,251,836 B1 | 6/2001 | Duncum et al. | |
| 6,436,877 B1 | 8/2002 | Duncum et al. | |
| 6,596,911 B2 | 7/2003 | Przybylinski et al. | |
| 2008/0299187 A1* | 12/2008 | Opheim et al. | 424/452 |
| 2010/0239603 A1* | 9/2010 | Wang et al. | 424/195.16 |
| 2010/0314312 A1* | 12/2010 | Baseeth et al. | 210/610 |
| 2011/0008876 A1* | 1/2011 | Scalzi et al. | 435/262.5 |
| 2011/0280852 A1* | 11/2011 | Miller | 424/94.1 |
| 2012/0178147 A1* | 7/2012 | Krajmalnik-Brown et al. | 435/252.4 |
| 2012/0199492 A1* | 8/2012 | Jin et al. | 205/413 |
| 2013/0189297 A1* | 7/2013 | Richards et al. | 424/195.15 |
| 2014/0128289 A1* | 5/2014 | Gordon et al. | 506/16 |
| 2014/0200204 A1* | 7/2014 | Gross et al. | 514/184 |

OTHER PUBLICATIONS

Rasche and White, "Mechanism for the Enzymatic Formation of 4-(beta-D-ribofuranosyl)aminobenzene 5'-phosphate During the Biosynthesis of Methanopterin." Biochemistry, Aug. 11, 1998;37(32):11343-51.

Siriwongrungson, "Homoacetogenesis as the Alternative Pathway for H2 Sink During Thermophilic Anaerobic Degradation of Butyrate Under Suppressed Methanogenesis." Water Res. Oct. 2007; 41 (18): 4204-10. Epub May 25, 2007.

Nagar-Anthal, "The Pterin Lumazine Inhibits Growth of Methanogens and Methane Formation." Archives of Microbiology. Aug. 1996, vol. 166, Issue 2, pp. 136-140.

Miller-Wolin, "Control of Rumen Methanogenesis by Inhibiting the Growth and Activity of Methanogens with Hydroxymtheylglutaryl-SCoa Inhibitors." International Congress Series, Jul. 2008, vol. 1293, pp. 131-137.

Wust, "Trophic Links Between Fermenters and Methanogens in a Moderately Acidic Fen Soil." Environ Microbiol. Jun. 2009; 11 (6):1395-409. doi:10.1111/j. 1462-2920.2009.01867.x.

Liu and Whitman (2008), "Metabolic, Phylogenetic, and Ecological Diversity of the Methanogenic Archaea." Annals of the New York Academy of Sciences, 1125: 171-189. doi: 10.1196/annals.1419. 019.

Conrad et al., "Phosphate Inhibits Acetotrophic Methanogensis on Rice Roots." Appl. Environ. Microbiol. 2000, 66 (2):828. doi: 10.1128/AEM.66.2.828-831.2000.

Dumitru and Ragsdale, "Mechanism of 4-(Beta-D-Ribofuranosyl)aminobenzene 5-Phosphate Synthase, a Key Enzyme in the Methanopterin Biosynthetic Pathway." The Journal of Biological Chemistry, 2004, vol. 279, No. 38, pp. 39389-39395, 2004.

Dumitru et al., "Targeting Methanopterin Biosynthesis to Inhibit Methanogensis." Appl. Environ. Microbiol., Dec. 2003, pp. 7236-7241. doi:10.1128/AEM.69.12.7236-7241.2003.

Ferry, "Bichemistry of Methanogenesis." Critical Reviews in Biochemistry and Molecualr Biology, 27(6):473-503 (1992).

Ferry, "Methanogenesis Biochemistry." Encyclopedia of Life Sciences. 2002 Macmillan Publishers.

Liu et al., "Chemical Inhibitors of Methanogenesis and Putative Applications." Appl. Microbiol. Biotechnol. 2011 89:1333-1340. doi: 10.1007/s00253-010-3066-5.

Miller and Wolin, "Inhibition of Growth of Methane-Producing Bacteria of the Ruminant Forestomach by Hydroxymethylglutaryl—SCoA Reductase Inhibitors." 2001, J. Dairy Sc. 84:1445-1448.

Reynolds and Colleran, "Evaluation and Improvement of Methods for Coenzyme F420 Analysis in Anaerobic Sludges." Journal of Microbiological Methods 7 (1987) 115-130.

Sharma et al., "Structure Modeling and Inhibitor Prediction of NADP Oxidoreductase Enzyme from Methanobrevibacter Smithii." 2011, Biomedical Informatics.

Zinder et al., "Selective Inhibition by 2-Bromoethanesulfonate of Methanogenesis from Acetate in a Thermophilic Anaerobic Digestor." Appl. Environ. Microbiol. Jun. 1984, pp. 1343-1345.

Bouwer and McCarty, "Transformations of 1- and 2-Carbon Halogenated Aliphatic Organic Compounds Under Methanogenic Conditions." Appl. Environ. Microbiol. Apr. 1983, pp. 1286-1294.

* cited by examiner

*Primary Examiner* — Chester Barry
(74) *Attorney, Agent, or Firm* — Douglas J. Ryder; Ryder, Lu, Mazzeo & Konieczny LLC

(57) ABSTRACT

This method of restricting methane production in methanogenic bacteria, by the use of the enzyme and coenzyme inhibitors, works during anaerobic reductive dechlorination. Various compounds such as, but not limited to, red yeast rice, vitamin B10 derivatives, and ethanesulfonates are utilized to disrupt these different enzyme and coenzyme systems responsible for the production of methane. This method affects the competition of the methanogen and halo bacteria for the organic hydrogen donors that are injected in the soil and groundwater system during the remediation process.

14 Claims, No Drawings

INHIBITION OF METHANE PRODUCTION DURING ANAEROBIC REDUCTIVE DECHLORINATION

FIELD OF THE INVENTION

The present invention relates to the use of various inhibitors of different enzyme and coenzyme systems responsible for the production of methane. The present invention utilizes various compounds including, but not limited to: red yeast rice, vitamin B10 derivatives, and ethanesulfonates to disrupt enzyme and coenzyme systems and limit the productivity of methanogens in producing methane.

BACKGROUND OF THE INVENTION

Halogenated volatile organic compounds (VOCs), including chlorinated aliphatic hydrocarbons (CAHs), are the most frequently occurring type of contaminant in soil and groundwater at Superfund and other hazardous waste sites in the United States. In 1996, the U.S. Environmental Protection Agency (EPA) estimated that cleanup of these sites will cost more than $45 billion over the next several decades.

CAHs are manmade organic compounds. They typically are manufactured from naturally occurring hydrocarbon constituents (methane, ethane, and ethene) and chlorine through various processes that substitute one or more hydrogen atoms with a chlorine atom, or selectively dechlorinate chlorinated compounds to a less chlorinated state. CAHs are used in a wide variety of applications, including uses as solvents and degreasers and in the manufacturing of raw materials. CAHs include such solvents as tetrachloroethene (PCE), trichloroethene (TCE), carbon tetrachloride (CT), chloroform (CF), and methylene chloride (MC). Historical management of wastes containing CAHs has resulted in contamination of soil and groundwater, with CAHs present at many contaminated groundwater sites in the United States. TCE is the most prevalent of those contaminants. In addition, CAHs and their degradation products, including dichloroethane (DCA), dichloroethene (DCE), and vinyl chloride (VC), tend to persist in the subsurface creating a hazard to public health and the environment.

The options available for a cost-effective and reliable technology to treat chlorinated hydrocarbon contaminants such as PCE, TCE, cis-1,2-dichlorethene (cis-1,2-DCE), and VC in groundwater have in recent years moved away from traditional pump-and-treat processes, especially in cases where:

Non-aqueous phase liquids (NAPLs), micro-emulsions or high concentration adsorbed materials are present leading to high dissolved phase concentrations.

Access to groundwater is restricted by surface structures or uses.

Local restrictions forbid the implementation of other available technologies such as air sparging or natural attenuation.

Pump-and-treat technologies have been applied, but have reached asymptotic removal rates.

Contamination is extensive and concentrations are too high for risk based closure but otherwise relatively low (typically 100-7500 ppb).

The migration of dissolved CAHs across property boundaries or into adjacent surface water presents a long-term remediation requirement.

The vertical migration of free phase CAHs (DNAPL) into underlying drinking water aquifers is a concern.

The environmental chemistry of each site in part determines the rate of biodegradation of chlorinated solvents at that site. The initial metabolism of chlorinated solvents such as chloroethenes and chloroethanes in ground water usually involves a biochemical process described as sequential reductive dechlorination. The occurrence of different types and concentrations of electron donors such as native organic matter, and electron acceptors such as oxygen and chlorinated solvents, determines to a large degree the extent to which reductive dechlorination occurs during the natural attenuation of a site.

Laboratory studies have shown that a wide variety of organic substrates will stimulate reductive dechlorination including acetate, propionate, butyrate, benzoate, glucose, lactate, methanol, and toluene. Inexpensive, complex substrates such as molasses, cheese whey, corn steep liquor, corn oil, hydrogenated cottonseed oil beads, solid food shortening, beef tallow, melted corn oil margarine, coconut oil, soybean oil, and hydrogenated soybean oil have the potential to support complete reductive dechlorination.

Reductive dechlorination only occurs in the absence of oxygen; and, the chlorinated solvent actually substitutes for oxygen in the physiology of the microorganisms carrying out the process. As a result of the use of the chlorinated solvent during this physiological process, it is at least in part dechlorinated. Remedial treatment technologies usually introduce an oxygen scavenger to the subsurface in order to ensure that this process would occur immediately.

Heterotrophic bacteria are often used to consume dissolved oxygen, thereby reducing the redox potential in the ground water. In addition, as the bacteria grow on the organic particles, they ferment carbon and release a variety of volatile fatty acids (e.g., acetic, propionic, butyric), which diffuse from the site of fermentation into the ground water plume and serve as electron donors for other bacteria, including dehalogenators and halorespiring species. An iron source usually provides substantial reactive surface area that stimulates direct chemical dechlorination and an additional drop in the redox potential of the ground water via chemical oxygen scavenging.

Bacteria generally are categorized by: 1) the means by which they derive energy, 2) the type of electron donors they require, or 3) the source of carbon that they require. Typically, bacteria that are involved in the biodegradation of CAHs in the subsurface are chemotrophs (bacteria that derive their energy from chemical redox reactions) and use organic compounds as electron donors and sources of organic carbon (organoheterotrophs). However, bacteria are classified further by the electron acceptor that they use, and therefore the type of zone that will dominate in the subsurface. A bacteria electron acceptor class causing a redox reaction generating relatively more energy, will dominate over a bacteria electron acceptor class causing a redox reaction generating relatively less energy.

Certain micro-organisms will assist in removing oxygen and nitrates from the applied systems. Halophiles are saltloving organisms that inhabit hypersaline environments. They include mainly prokaryotic and eukaryotic microorganisms with the capacity to balance the osmotic pressure of the environment and resist the denaturing effects of salts. Among halophilic microorganisms are a variety of heterotrophic and methanogenic archaea; photosynthetic, lithotrophic, and heterotrophic bacteria; and photosynthetic and heterotrophic eukaryotes. One the other hand, methanogens, play a vital environmental role in anaerobic environments, since they remove excess hydrogen and fermentation products that have been produced by other forms of anaerobic respiration. Methanogens typically thrive in environments in which all electron acceptors other than $CO_2$ (such as oxygen, nitrate, trivalent iron, and sulfate) have been depleted.

Based on thermodynamic considerations, reductive dechlorination will occur only after both oxygen and nitrate have been depleted from the aquifer since oxygen and nitrate are more energetically favorable electron acceptors than chlorinated solvents. Almost any substrate that can be fermented to hydrogen and acetate can be used to enhance reductive dechlorination since these materials are used by dechlorinating microorganisms. However, hydrogen is also a substrate for methanogenic bacteria that converts it to methane. By utilizing hydrogen, the methanogens compete with dechlorinating microbes.

Ultimately, the inhibition of methanogenesis will result into lower methane production, which positively affects numerous environmental aspects of major concern, and will also help dehalogenating bacteria to more effectively utilize the environmental conditions that promote reductive dechlorination or chlorinated volatile organic compounds (CVOCs) in in-situ remediation processes.

Therefore, there is a need in the art for a method of inhibiting enzyme and coenzyme systems that are responsible for producing methane during the anaerobic reductive dechlorination process.

SUMMARY OF THE INVENTION

In order to solve the need in the art for a method of inhibiting enzyme and coenzyme systems that are responsible for producing methane during the anaerobic reductive dechlorination process, the present invention has been devised.

This invention provides different methods of inhibition of methane production from methanogenic bacteria by depressing the action of various enzymes and coenzymes that play a key role in the methane production. Various enzymes and coenzymes are targeted in the current invention. The inhibitors used are found to be harmless for the rest of the bacteria that are present in the system.

This method of restricting methane production in methanogenic bacteria, by the use of the enzyme inhibitors, can be very useful during in-situ remediation of chlorinated solvents. This method is expected to positively affect the competition of the methanogen and halo bacteria for the organic hydrogen donors that are injected in the soil and groundwater system during the remediation process. This method also provides an alternative approach for the decrease of the emission levels of methane, which is considered a major greenhouse gas.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENTS

Biological methane formation is a microbial process catalyzed by methanogens. The methanogenic pathways of all species have in common the conversion of a methyl group to methane; however the origin of the methyl group varies. Most species are capable of reducing carbon dioxide ($CO_2$) to a methyl group with either a molecular hydrogen ($H_2$) or formate as the reductant. Methane production pathways in methanogens that utilize $CO_2$ and $H_2$, involve specific methanogen enzymes, which catalyze unique reactions using unique coenzymes. Biosynthetic enzyme, 4-(β-D-ribofuranosyl)aminobenzene-5"-phosphate (β-RFA-P) synthase, is a key enzyme that catalyzes the first step of in methanopterin biosynthesis. This enzyme catalyzes the condensation between para-aminobenzoic acid (pABA) and 5-phospho-α-D-ribosyl-1-pyrophosphate (PRPP) with concomitant formation of β-RFA-P, $CO_2$, and inorganic pyrophosphate (PPi). This enzyme is a phosphoribosyltransferase and a decarboxylase and forms a C-riboside, which is unique among phosphoribosyltransferases and pABA-dependent enzymes.

β-RFA-P synthase is an early step in the biosynthesis of tetrahydromethanopterin ($H_4MPT$), which is a modified folate that is of central importance in growth and energy metabolism of methanogens.

Methanofuran and $H_4MPT$, function as one-carbon carriers in the reversible reduction of $CO_2$ to a methyl group. $H_4MPT$ is involved in multiple steps in methane formation, as in one carbon reactions involved in amino acid and nucleotide metabolism. Even though $H_4MPT$ is found in Archaea and one class of Bacterium (e.g. *Methylobacterium extorquens*), the biosynthetic pathway for these two folates (folate and methanopterin) is different, suggesting that they play different functional roles in the physiology of the cell (Dumitru and Ragsdale, 2004).

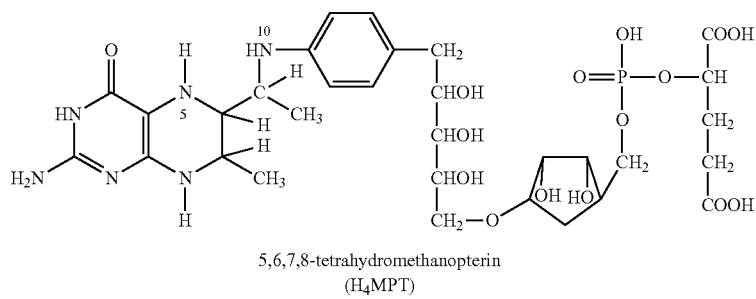

5,6,7,8-tetrahydromethanopterin (H₄MPT)

Structure of Tetrahydromethanopterin

Coenzyme $F_{420}$ or 8-hydroxy-5-deazaflavin, is a two electron transfer coenzyme that is involved in redox reactions in methanogens in many Actinobacteria, and sporadically in other bacterial lineages. It occurs at varying levels in all methanogenic species and has also been identified in *Streptomyces griseus* and *Anacystis nidulans*. At least four different forms of the coenzyme have been described, all containing a deazariboflavin chromophore with an extended side-chain composed of two, three, four or five glutamic acid residues. Coenzyme $F_{420-2}$ (i.e., with a side-chain consisting of two glutamic acid residues) appears to be the coenzyme form present in hydrogenotrophic methanogens, whereas methylotrophic species contain coenzymes $F_{420-4}$ and $F_{420-5}$ (Reynolds and Colleran, 1987).

One of the characteristics of $F_{420}$ is that it acts as an electron donor for two steps in the reduction of $CO_2$ to a methyl group. The $F_{420}$-dependent NADP oxidoreductase enzyme from *Methanobrevibacter smithii* catalyzes the important electron transfer step during methanogenesis between NADP+ and $F_{420}$. During the reaction, NADP is reduced to NADPH by accepting one or more hydrides (H⁻) from $F_{420}$. This is an important step of methane formation in methanogen bacteria such as *M. smithii*. Therefore, the NADP oxidoreductase enzyme plays a vital role in the formation of methane (Sharma et al. 2011).

Structure of Coenzyme $F_{420}$

Coenzyme M (CoM) is the smallest cofactor known in nature. This cofactor is methylated on the sulfhydryl group, forming $CH_3$-S-CoM, the substrate for the methylreductase which catalyzes the terminal step in all methanogenic pathways. Coenzyme B is the second substrate for methyl-coenzyme M reductase, and as a consequence of the reaction, forms the heterodisulfide complex with CoM (CoB-S-S-CoM) (Ferry, 2002). 3-hydroxy-3-methylglutaryl coenzyme A (HMG-CoA) reductase, is also another enzyme that is very critical in methane production in *Methanobrevibactor* strains, since Archaea are the only bacteria known to possess biosynthetic HMG-CoA reductase (Miller and Wollin, 2001).

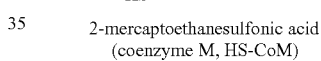

2-mercaptoethanesulfonic acid (coenzyme M, HS-CoM)

Structure of Coenzyme M (CoM)

The reduction of $CO_2$ to $CH_4$ with $H_2$ as the electron donor (Reaction 1) is the pathway of methanogenesis that this invention is focused on.

$$4H_2 + CO_2 \rightarrow CH_4 + 2H_2O, \Delta G° = -130.4 \text{ kJ/mol } CH_4 \quad (1)$$

The $CO_2$-reduction pathway is observed in the presence of *Methanobacterium thermoautotrophicum* strains (Ferry, 2002).

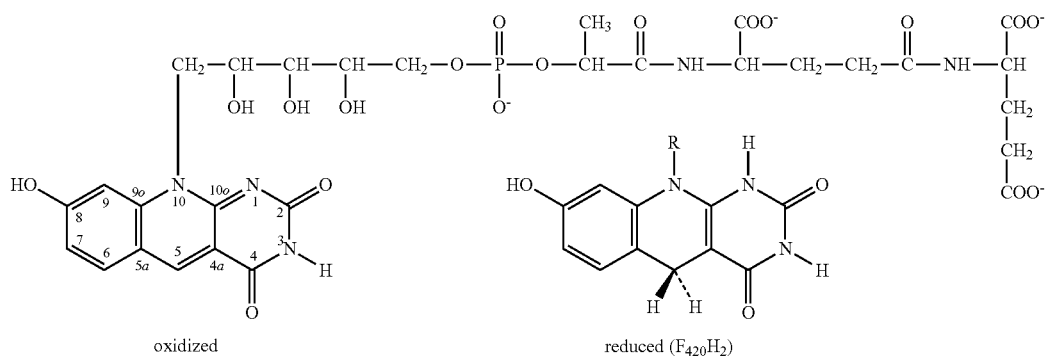

coenzyme $F_{420}$ ($F_{420}$)

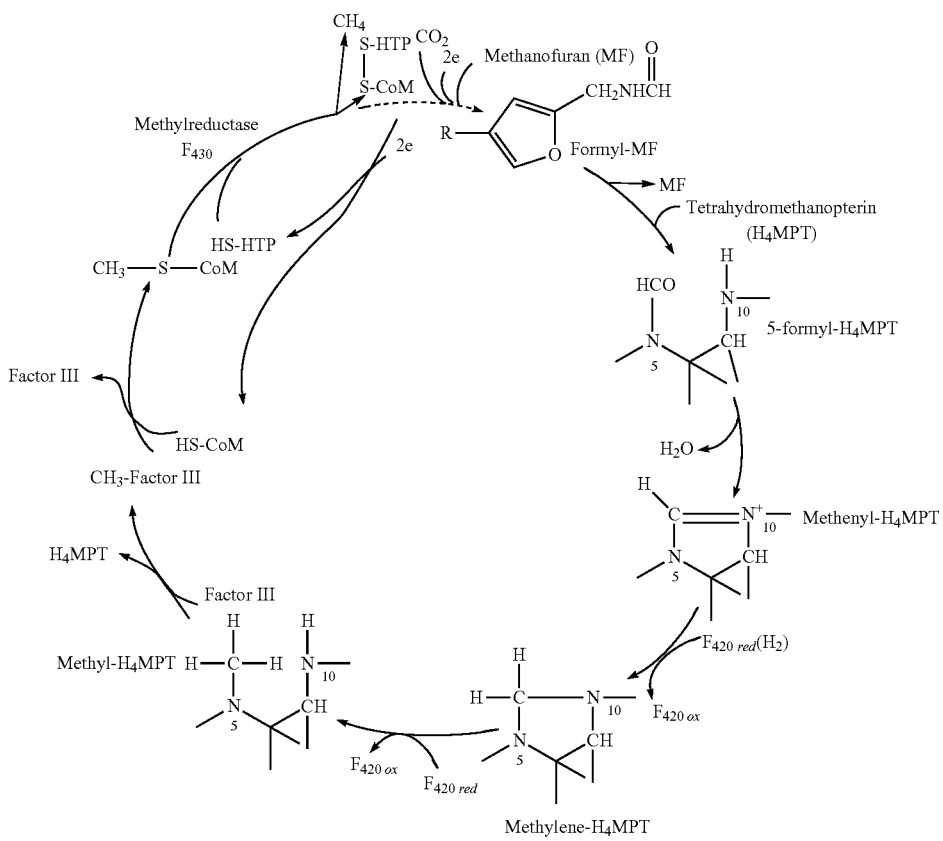

The Pathway of CO$_2$-Reduction to CH$_4$

The steps are that are followed during the reduction of CO$_2$ to CH$_4$ are the following: first carbon dioxide is reduced to the formyl level, then the formyl group is reduced to the formaldehyde level, on the following step the methylene group is reduced to the methyl level and finally the methyl group is converted to methane. All four of the reductive steps are briefly described below (Ferry, 1992).

1. Reduction of Carbon Dioxide to the Formyl Level

The reduction of CO$_2$ to the formyl level is catalyzed by formyl-methanofuran dehydrogenase (FMF). FMF is the first stable intermediate in the pathway. Enzyme activity in the reverse direction is linked to the reduction of either methylviologen or coenzyme F$_{420}$ in all extracts of *M. thermoautotrophicum* strain.

2. Reduction of the Formyl Level to the Formaldehyde Level

Prior to reduction, the formyl group is transferred to 5,6,7,8-tetrahydromethanopterin, as shown in Reaction 2, and then converted to the methenyl derivative by the dehydrating cyclization as shown in Reaction 3.

$$\text{FMF} + \text{H}_4\text{MPT} \rightarrow \text{5-Formyl-H}_4\text{MPT} + 2\text{MF}, \quad \Delta G^\circ = -4.4 \text{ kJ/mol} \tag{2}$$

$$\text{5-Formyl-H}_4\text{MPT} + \text{H}^+ \rightarrow \text{5,10-methenyl-H}_4\text{MPT}^+ + \text{H}_2\text{O}, \quad \Delta G^\circ = -4.6 \text{ kJ/mol} \tag{3}$$

The reduction of 5,10-methenyl-H$_4$MPT$^+$ to the formaldehyde level with reduced coenzyme F$_{420}$ is shown in Reaction 4.

$$\text{5,10-methenyl-H}_4\text{MPT}^+ + \text{F}_{420}\text{H}_2 \rightarrow \text{5,10-methylene-H}_4\text{MPT} + \text{F}_{420} + \text{H}^+, \quad \Delta G^\circ = +6.5 \text{ kJ/mol} \tag{4}$$

Coenzyme F$_{420}$ is an obligate two-electron carrier as mentioned above (redox potential $\sim$−350 mV) that donates or accepts a hydride ion. The disappearance of the 5,10-methenylene-H$_4$MPT dehydrogenase activity results into increasing dependence on F$_{420}$ as an electron acceptor during the purification procedure or upon exposure to the air.

3. Reduction of the Methylene Group to the Methyl Level

The 5,10-methylene-H$_4$MPT reductase utilizes reduced F$_{420}$ (F$_{420}$H$_2$) as the physiological electron donor for Reaction 5.

$$\text{5,10-methylene-H}_4\text{MPT} + \text{F}_{420}\text{H}_2 \rightarrow \text{5-methyl-H}_4\text{MPT} + \text{F}_{420}, \quad \Delta G^\circ = -5.2 \text{ kJ/mol} \tag{5}$$

This reaction proceeds in either direction; however the physiologically relevant methylene reduction is thermodynamically favored. Since H$_2$ is the source of electrons (Reaction 6), the reduction is exergonic and therefore could be associated with the generation of a primary electrochemical potential.

$$\text{5,10-methylene-H}_4\text{MPT} + \text{H}_2 \rightarrow \text{5-methyl-H}_4\text{MPT}, \quad \Delta G^\circ = -14 \text{ kJ/mol} \tag{6}$$

4. Conversion of the Methyl Group to Methane a. Transfer of the Methyl Group to Coenzyme M Prior to the reduction, the methyl group of 5-methyl-H$_4$MPT is transferred to Coenzyme M (HS-CoM), as shown in Reaction 7.

$$\text{5-methyl-H}_4\text{MPT} + \text{HS-CoM} \rightarrow \text{CH}_3\text{-S-CoM} + \text{H}_4\text{MPT}, \quad \Delta G^\circ = -29.7 \text{ kJ/mol} \tag{7}$$

b. Reductive Demethylation of CH$_3$-S-CoM to Methane

The CH$_3$-S-CoM methylreductase catalyzes Reaction 8. In the final reductive step of the pathway, CoM-S-S-HTP is reduced to the respective sulhydryl cofactors (Reaction 9).

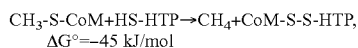
(8)

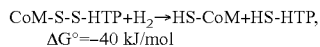
(9)

This invention provides additional embodiments for the inhibition of the enzymes and coenzymes, which as mentioned above are integral parts of the methanogenesis process. The targeted enzymes is methanopterin, and the targeted coenzymes are coenzyme $F_{420}$ and coenzymes A and M.

Biosynthetic enzyme 4-(β-D-ribofuranosyl)aminobenzene-5'-phosphate (β-RFA-P) synthase, catalyzes the first step in methanopterin biosynthesis. The reduced form of methanopterin, $H_4MPT$, is involved in multiple steps in methanogenesis; it also replaces the functions of tetrahydrofolic acid, the predominant one-carbon carrier in eukaryotes and bacteria. Given the importance of $H_4MPT$ in growth and in energy production by methanogens, the inhibition of RFA-P synthase should specifically halt methanopterin biosynthesis and thereby preclude methanogenesis without adversely affecting the metabolism of other bacterial. Many researchers have performed studies that support the above hypothesis (Dumitru et al. 2003). During the first step of methanopterin biosynthesis, RFA-P synthase catalyzes the conversion of phosphoribosylpyrophosphate (PRPP) and pABA to $CO_2$, inorganic pyrophosphate, and β-RFA-P.

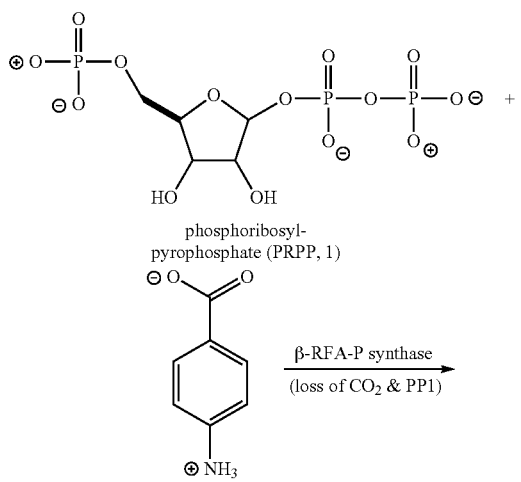

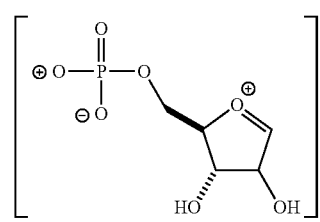

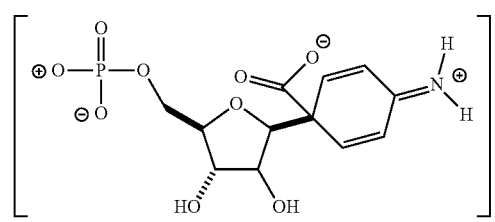

The Reaction Catalyzed by RFA-P Synthase

Some researchers partially purified and characterized the methanogenic RFA-P synthase, and the enzyme from *Archaeoglobus fulgidus* was purified to homogeneity, cloned and heterologously overexpressed. The reaction proceeds via the oxycarbenium intermediate and its adduct with pABA (Rasche and White, 1998). Most importantly though, other research groups (Dumitru et al. 2003) focused on designing competitive inhibitors that are structural analogs of pABA. Analogs of pABA that inhibit RFA-P synthase are highly selective because the amino group is the nucleophile in most pABA-dependent reactions, while the ring carbon 4 is the nucleophile in the RFA-P synthase-catalyzed reaction.

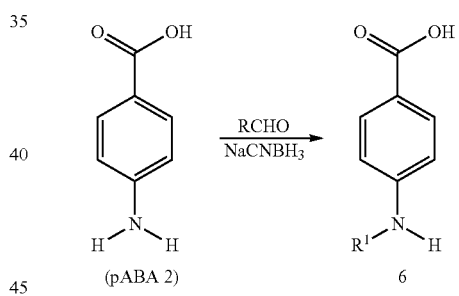

Analogs of pABA

The inhibitors presented by Dumitru et al. (2003) impair RFA-P synthase activity and arrest methanogenesis in pure cultures of methanogens. Supplying an excess of the natural substrate pABA to the culture relieves the inhibition, suggesting that RFA-P synthase is the cellular target. The inhibitors do not adversely affect the growth of acetogenic bacteria.

It has to be noted that pABA, is also more widely known as vitamin B10. Vitamin B10 is part of the vitamin B complex and is considered to be a water soluble vitamin. pABA is a component of pteroylglutamate; it was once considered a vitamin and named vitamin B-x because it serves as a provitamin for some bacteria.

Dumitru et al. (2003) synthesized various inhibitors, all of which were N-substituted derivatives of pABA, and determined their inhibition constants with PFA-P synthase. The results suggested that the pABA binding site in RFA-P synthase has a relatively large hydrophobic pocket near the amino group. Each of the pABA analogs was tested for their ability to inhibit methanogenesis and the growth of the methanogen *M. marburgensis* (formerly known as *M. thermoautotrophicum*). Insignificant amounts of methane were measured in the headspace of *M. marburgensis* cultures whose growth was completely inhibited. At 100 nM, the most potent inhibitor currently, 4-[(2-pyridylmethyl)amino]benzoic acid, completely arrests the growth of methanogens and the formation of methane by *M. marburgensis*. Inhibition is fully reversed by supplementing the medium with pABA, indicating a competitive interaction between pABA and the inhibitor at the cellular target, which is most likely RFA-P synthase.

Acetogenesis is an anaerobic and hydrogenotrophic bacterial process that competes with methanogenesis in many anaerobic habitats. Each of the inhibitors was tested for its effect on the growth of the acetogenic bacterium *M. thermoacetica*. Methanopterin is not required for survival of bacteria; accordingly, none of the RFA-P synthase inhibitors described here affect the growth of *M. thermoacetica* at concentrations as high as 1 mM (Dumitru et al. 2003).

The effect of the inhibitors was tested on methane formation and volatile fatty acids (VFA) production. Methane production is completely inhibited by 5 mM 4-(ethylamino)benzoate or 9 mM 4-(isopropylamino)benzoate. 5 mM of 4-(2-hydroxyethylamino)benzoate inhibited methane production to 2.5% of the control level. As a control, 1 mM bromoethanesulfonate, an inhibitor of methyl-coenzyme M reductase, completely inhibited (P<0.01) methane production in all experiments (Dumitru et al. 2003).

The effect of some of the effective inhibitors on VFA production was also tested. VFA production was not depressed by adding an RFA-P synthase inhibitor at concentrations that completely block methanogenesis. For example, when 7 mM 4-ethylaminobenzoate was added to the artificial rumen system, acetate (P<0.05) and propionate (P<0.10) levels were elevated relative to the controls unexposed to the inhibitors. These results were consistent with the studies with pure cultures of acetogenic bacteria and indicate that the inhibitors do not adversely affect other bacteria (Dumitru et al. 2003).

Sharma et al. (2011) tested the potential inhibitory effect that Lovastatin and Compactin (Mevastatin) had on the $F_{420}$-dependent NADP oxidoreductase enzyme from *M. smithii*, during methanogenesis. Based on the results of their study it was found that both Lovastatin and Compactin (Mevastatin) compounds were effective as potential inhibitors of the $F_{420}$-dependent NADP oxidoreductase protein.

Lovastatin ($C_{24}H_{36}O_5$) is a secondary product of idiophase (secondary phase) of growth of fungi and is an inhibitor of enzyme 3-hydroxy-3-ethylglutaryl coenzyme A (HMG-CoA) reductase, a key enzyme in cholesterol production pathway in humans. There is a similarity between cholesterol formation in human and cell membrane formation in the Archaea as the lipid side of phospholipids in the cell membrane of Archaea is isoprenoid chains. Isoprenoid formation is an intermediate step of cholesterol production pathway (Mevalonate pathway) and HMG-CoA reductase is also a key enzyme for its production. Therefore, as an inhibitor of HMG-CoA reductase, lovastatin suppresses isoprenoid production and thus cholesterol synthesis and membrane formation in the Archaea. Wolin and Miller (2005) showed that lovastatin significantly reduced growth and activity of pure methanogenic bacteria without any negative effect on cellulolytic bacteria.

As mentioned above, $F_{420}H_2$-NADP is one of the coenzymes that act during the catalysis of the electron transfer step between $NADP^+$ and $F_{420}$, reducing NADP to NADPH with the acceptance of one or more hydrides ($H^-$) from $F_{420}$.

Sharma et al. (2011) determined a 3D model structure of the $F_{420}$-dependent NADP oxidoreductase from *M. smithii*. Based on their protein model of $F_{420}$-dependent NADP oxidoreductase enzyme, they detected that these residues are making a ligand binding site pocket, and after further studies they found that ligand $F_{420}$ binds at the protein cavity. The inhibitor compounds Lovastatin and Compactin (Mevastatin) show more affinity for the model protein as compare to the natural ligand $F_{420}$. They share the same cavity as by $F_{420}$ and surround by similar residues. In other words the inhibitor compounds Lovastatin and Compactin (Mevastatin) were very effective in blocking the activity site for methane production since the enzyme was unable to bind with the substrate, resulting in decreased methane production. Lovastatin is a fungal metabolite isolated from cultures of *Aspergillus terreus* and Compactin (Mevastatin) is an antifungal metabolite from *Penicillium brevicopactum*. Sharma et al. (2011) establish that Lovastatin and Compactin (Mevastatin) may act as potent inhibitor for the $F_{420}$-dependent NADP oxidoreducatse protein in order to block its active site.

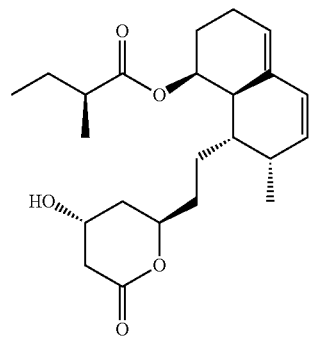 [SMILES: CC[C@H](C)C(=O)O[C@H]1CCC=C2C=C[C@H](C)[C@H](CC[C@@H]3C[C@@H](O)CC(=O)O3)[C@H]21]

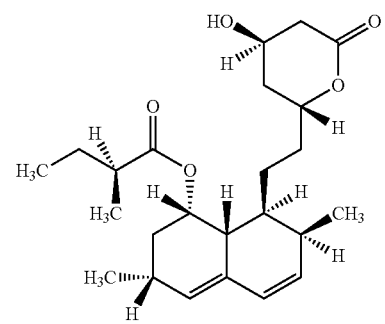 [SMILES: CC[C@@H](C)C(=O)O[C@H]1C[C@@H](C)C=C2C=C[C@H](C)[C@H](CC[C@@H]3C[C@@H](O)CC(=O)O3)[C@H]21]

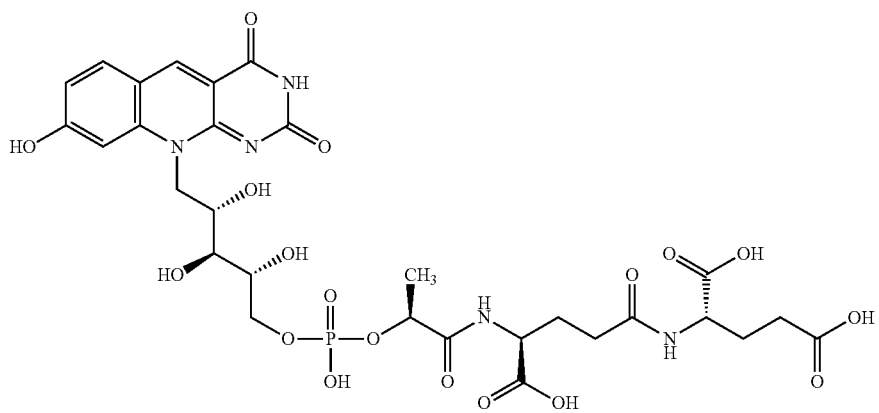 [SMILES: C[C@H](OP(=O)(O)OC[C@@H](O)[C@@H](O)[C@@H](O)Cn1c2nc(=O)[nH]c(=O)c-2cc2ccc(O)cc21)C(=O)N[C@@H](CCC(=O)N[C@@H](CCC(=O)O)C(=O)O)C(=O)O]

Coenzyme F420

Structure of Compactin (Mevastatin), Lovastatin and F$_{420}$

Researchers have found that red yeast rice, which is an Asian dietary staple made by fermenting yeast (*Monascus purpureus*) on rice, contains active ingredients of the statin drugs such as Lovastatin. Thus, studies have shown that red yeast rice can successfully inhibit the key enzyme hydroxymethylglutaryi-SCoA (HMG-CoA) reductase, resulting in the inhibition of methanogenic activity.

Miller and Wolin (2001) also used Lovastatin to inhibit the formation of the key precursor mevalonate. Mevalonate is formed by reduction of hydroxymethylglutaryi-SCoA (HMG-CoA). Based on their results they found that lovastatin inhibited the growth of *Methanobrevibacter* and CH$_4$ production. In fact 4 nmol/ml of culture medium resulted in 50% inhibition of growth and concentrations ≥10 nmol/ml of culture medium completely inhibited growth. Methane formation was also significantly inhibited. At the same time the populations of the nonmethanogens were not affected.

Coenzyme M (CoM; HSCH$_2$CH$_2$SO$_3^-$) is a cofactor which is found in all methanogens but not in other bacteria or archaea (Liu and Whitman 2008). CoM is involved in the terminal step of methane biosynthesis, where the methyl group carried by CoM is reduced to methane by methyl-CoM reductase. The methanogenic inhibitors involved in this group usually include 2-bromoethanesulfonate (BES), 2-chloroethanesulfonate (CES), 2-mercaptoethanesulfonate (MES), and lumazine (Liu et al. 2011). These inhibitors can competitively constrain the methyl transfer reaction at the terminal reductive step during methane formation in methanogens using H$_2$ and CO$_2$. Under normal circumstances, these compounds can inhibit all the groups of methanogens at relatively low concentrations. A traditional structural analog of CoM and BES has been widely used and considered as a methanogen-specific inhibitor in microbiological studies. Conrad et al. (2000) reported that 10 mM BES is the optimum concentration to inhibit the anaerobic methanogens in the rice roots systems. In the thermophilic environment of an anaerobic digester, complete inhibition of the methanogenesis is achieved with the use of at least 50 mM BES. A higher BES concentration is needed for the inhibition of the hydrogenotrophic methanogens than the acetoclastic methanogens (Zinder et al. 1984); however, a similar system requires, only 10 mM of BES in order to inhibit the methanogenesis process (Siriwongrungson et al. 2007). Other studies show that concentrations of 5-20 mM in the soil (Wüst et al. 2009) are really effective in inhibiting methanogenesis. MES and CES also have similar inhibition effects and were used to decrease the methanogenic activity in the continuous-flow methanogenic fixed-film column (Bouwer and McCarty 1983). Various reports show that the pterin compound lumazine[2,4-(1H, 3H)-pteridinedione] completely inhibited the growth of several methanogenic archaea at a concentration of 0.6 mM and was bactericidal for *M. thermoautotrophicum* strain Marburg (Nagar-Anthal et al. 1996).

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method for accelerating biotic dehalogenation of groundwater and soils affected by chlorinated aromatic and aliphatic compounds, comprising the step of:
   inhibiting growth of methane-producing bacteria, by injecting one or more inhibitory factors into the groundwater or soil, the inhibitory factors including red yeast rice, to target one or more enzymes and coenzymes that are responsible for production of methane, the one or more enzymes and coenzymes including Coenzyme F420 (8-hydroxy-5-deazaflavin); therefore reducing the methane-producing bacteria which compete with halorespiring bacteria during an anaerobic reductive dechlorination process in soil and groundwater media.

2. The method of claim 1, wherein the methane-producing bacteria to be inhibited are located in the soil and groundwater media.

3. The method of claim 1, wherein the one or more enzymes and coenzymes further include 3-hydroxy-3-ethylglutaryl coenzyme A (HMG-CoA) reductase.

4. The method of claim 3, wherein the one or more inhibitory factors for the 3-hydroxy-3-ethylglutaryl coenzyme A (HMG-CoA) reductase include lovastatin, a secondary product of idiophase (secondary phase) of growth of fungi.

5. The method of claim 1, wherein the one or more inhibitory factors for the Coenzyme F420 (8-hydroxy-5-deazaflavin) include lovastatin.

6. The method of claim 1, wherein the injecting inhibitory factors into the groundwater or soil includes injecting a predetermined amount of the inhibitory factors in combination with fermentable substrates.

7. The method of claim 6, wherein the fermentable substrates are selected from the group consisting of acetate, propionate, butyrate, benzoate, glucose, lactate, methanol, toluene, molasses, cheese whey, corn steep liquor, corn oil, hydrogenated cottonseed oil beads, solid food shortening, beef tallow, melted corn oil margarine, coconut oil, soybean oil, and hydrogenated soybean oil.

8. A method for accelerating biotic dehalogenation of groundwater and soils affected by chlorinated aromatic and aliphatic compounds, the method comprising:
    injecting one or more inhibitory factors including red yeast rice into the groundwater or the soils to target one or more enzymes and coenzymes, including Coenzyme F420 (8-hydroxy-5-deazaflavin), that are responsible for production of methane in order to inhibit growth of methane-producing bacteria which compete with halorespiring bacteria during an anaerobic reductive dechlorination process in the groundwater and the soils.

9. The method of claim 8, wherein the one or more inhibitory factors further include lovastatin, a secondary product of idophase (secondary phase) of growth of fungi.

10. The method of claim 8, wherein the injecting one or more inhibitory factors into the groundwater or the soils is performed in-situ.

11. The method of claim 8, wherein the one or more enzymes and coenzymes further include 3-hydroxy-3-ethyl-glutaryl coenzyme A (HMG-CoA) reductase.

12. The method of claim 8, wherein the one or more enzymes and coenzymes further include 4-($\beta$-D-ribofuranosyl)aminobenzene-5"-phosphate ($\beta$-RFA-P) synthase.

13. The method of claim 8, wherein the injecting one or more inhibitory factors includes injecting the one or more inhibitory factors in combination with fermentable substrates.

14. The method of claim 13, wherein the fermentable substrates include at least some subset of acetate, propionate, butyrate, benzoate, glucose, lactate, methanol, toluene, molasses, cheese whey, corn steep liquor, corn oil, hydrogenated cottonseed oil beads, solid food shortening, beef tallow, melted corn oil margarine, coconut oil, soybean oil, hydrogenated soybean oil, and vegetable oil.

* * * * *